(12) United States Patent
Trivedi et al.

(10) Patent No.: US 9,023,323 B2
(45) Date of Patent: May 5, 2015

(54) ORAL COMPOSITIONS FOR PREVENTION AND REDUCTION OF BACTERIAL ADHESION TO ORAL SURFACES

(75) Inventors: Harsh M. Trivedi, Somerset, NJ (US); Tao Xu, East Brunswick, NJ (US); Kimberlee Panaligan, Parlin, NJ (US)

(73) Assignee: Colgate-Palmolive Company, New York, NY (US)

( * ) Notice: Subject to any disclaimer, the term of this patent is extended or adjusted under 35 U.S.C. 154(b) by 40 days.

(21) Appl. No.: 11/244,663

(22) Filed: Oct. 6, 2005

(65) Prior Publication Data

US 2006/0134018 A1 Jun. 22, 2006

Related U.S. Application Data

(60) Provisional application No. 60/636,788, filed on Dec. 16, 2004, provisional application No. 60/636,787, filed on Dec. 16, 2004.

(51) Int. Cl.
  *A61K 8/00* (2006.01)
  *A61K 8/66* (2006.01)
  *A61K 8/49* (2006.01)
  *A61Q 11/00* (2006.01)

(52) U.S. Cl.
  CPC .............. *A61K 8/66* (2013.01); *A61K 8/4926* (2013.01); *A61Q 11/00* (2013.01)

(58) Field of Classification Search
  None
  See application file for complete search history.

(56) References Cited

U.S. PATENT DOCUMENTS

| | | | |
|---|---|---|---|
| 3,194,738 A | 7/1965 | Harrisson et al. | |
| 4,071,614 A * | 1/1978 | Grimm, III | 424/49 |
| 4,082,841 A * | 4/1978 | Pader | 424/50 |
| 5,370,864 A | 12/1994 | Peterson et al. | |
| 5,670,142 A | 9/1997 | Rubin | |
| 5,776,435 A | 7/1998 | Gaffar et al. | |
| 6,241,973 B1 | 6/2001 | Rinne | |
| 6,379,654 B1 | 4/2002 | Gebreselassie et al. | |
| 6,447,758 B1 * | 9/2002 | Carale et al. | 424/54 |
| 6,652,841 B1 * | 11/2003 | Brown et al. | 424/49 |
| 6,692,726 B1 * | 2/2004 | Morgan et al. | 424/50 |
| 6,740,311 B2 | 5/2004 | White, Jr. et al. | |
| 2003/0206874 A1 | 11/2003 | Doyle et al. | |
| 2003/0211053 A1 * | 11/2003 | Szeles et al. | 424/50 |
| 2004/0042977 A1 | 3/2004 | Williams et al. | |
| 2004/0156796 A1 | 8/2004 | Morgan et al. | |

FOREIGN PATENT DOCUMENTS

| | | | |
|---|---|---|---|
| CA | 959 764 | 12/1974 | |
| CA | 2590211 | 6/2006 | |
| EP | 1551361 | 9/2010 | |
| FR | 2 036 | 9/1963 | |
| JP | 63215668 | 9/1988 | |
| JP | 10077276 | 3/1998 | |
| WO | WO 93/24142 * | 12/1993 | A61K 37/54 |
| WO | WO03/094877 | 11/2003 | |
| WO | 2004019898 | 3/2004 | |
| WO | WO2004/100913 | 11/2004 | |

OTHER PUBLICATIONS

Mukherjee. "Study of anticalculus agents". Journal of Periodontal Research. 1969. 4(1), pp. 26-35. (Abstract only).
Miller et al. "Enzyme separation techniques for the study of growth of cells from layers of bovine dental pulp". In Vitro. 1976. 12(8), pp. 580-588. (Abstract only).
Herles, S. et al. (1994). "Chemostat flow cell system: an in vitro model for the evaluation of antiplaque agents." *J Dent Res* 73(11): 1748-55.
Quesnel, L.B., et al. (1978). "Synergism between Chlorhexidine and Sulphadiazine." *Journal of Applied Bacteriology* 45: 397-405.
Shea, Catherine & Williamson, J. Chad. "Rapid Analysis of Bacterial Adhesion in a Microplate Assay". *BioTechniques.* (1990) vol. 8, No. 9.
Froning et al. "Characteristics of bone . . . " Poultry Science, vol. 60, 1981, pp. 1443-1447.
Dictionary of Chemistry and Chemical Engineering, 2003, Chemical Industry Press, 1st ed., p. 1549.
Berg et al., 2001, "Proteolytic degradation of oral biofilms in vitro and in vivo: potential of proteases originating from *Euphausia superba* for plaque control," European J. Oral Sci. 109(5):316-324.
Ling et al., 1998, "Making and Application of Papain," Papain and Papaya Cultivation, Chapter 9, China Agriculture Press, 1st ed., pp. 100-110.

* cited by examiner

*Primary Examiner* — Snigdha Maewall
(74) *Attorney, Agent, or Firm* — Howard C. Lee

(57) ABSTRACT

The present invention encompasses an oral composition containing an anti-adhesion agent, preferably a cysteine protease and most preferably ficin. In another aspect, the cysteine protease is in combination with one or more ingredients, such as antibacterial agent and surfactant. The anti-adhesion agent mitigates interaction between a subject oral cavity and plaque-forming materials.

10 Claims, No Drawings

ORAL COMPOSITIONS FOR PREVENTION AND REDUCTION OF BACTERIAL ADHESION TO ORAL SURFACES

CROSS REFERENCE TO RELATED APPLICATIONS

This application claims priority to U.S. Provisional Patent Application Ser. Nos. 60/636,788 and 60/636,787 each filed 16 Dec. 2004, the contents of both which are incorporated herein by reference.

BACKGROUND OF THE INVENTION

Dental plaque or plaque biofilm is a soft deposit that forms on surfaces of the oral cavity, such as tissue and teeth, and is comprised of an accumulation of bacteria and salivary as well as food by-products. Plaque adheres tenaciously at the points of irregularity or discontinuity (e.g., to calculus, at the gum line, on tongue surface and within crevices, and the like). Besides being unsightly, plaque is implicated in the occurrence of gingivitis and other forms of periodontal disease.

For the most part, the bacteria in the oral cavity are a part of a protective biofilm that essentially renders them resistant to most treatments. Few people clean their tongue after brushing, even though it's been shown that as much as 50 percent of the mouth's bacteria can be found here. Additionally, for many people, brushing or scraping the tongue is difficult because of the gag reflex. Therefore, cleaning the tongue non-mechanically is highly desirable for those who are unable to do so with a mechanical device.

A wide variety of agents have been suggested in the art to retard plaque formation and the oral infections and dental disease associated with plaque formation.

In spite of the extensive prior art relating to antibacterial dentifrice and oral compositions, there is still a need in the art to formulate a product capable of enhanced effect in the retardation of bacterial plaque accumulation.

BRIEF SUMMARY OF THE INVENTION

The present invention encompasses an oral composition containing an anti-adhesion agent, preferably a cysteine protease and most preferably ficin. In another aspect, the cysteine protease is in combination with one or more ingredients, such as antibacterial agent and surfactant. The anti-adhesion agent mitigates interaction between an oral cavity surface and plaque-forming materials, such as bacteria.

DETAILED DESCRIPTION OF THE INVENTION

The present invention provides a specific type of enzyme for preventing, interrupting, or at least inhibiting the binding or adhesion or attachment of plaque-forming material, including biologic material, chemicals, microorganisms, and bacteria to surfaces of an oral cavity. The enzymes for use in the present invention inhibit build-up of bacterial layer that would result in plaque build-up. It is believed that such enzymes function by attaching to oral surfaces, including soft tissue, and, thus, inhibit the growth of plaque or its further growth. The terms "anti-adhesion" and "anti-attachment" are used herein interchangeably. Suitable enzymes for use in the invention include anti-adhesion protease enzymes, desirably cysteine protease and are most desirably selected from the group ficin, papain and krillase. Preferably, the anti-adhesion agent comprises ficin and one or more other enzymes, such as other anti-adhesion enzyme(s) or another type of enzyme, such as bromelain, chymotrypsin, alcalase, amalysecs, glucose oxidase, cellusases, lipases, and/or other protease besides the anti-adhesion cysteine protease.

Ficin for use in the invention may be obtained by any means from the Preferably, it is obtained by drying and filtering the latex from the genus *Ficus*, including *Ficus glabrata*.

The amount of anti-adhesion agent present in the composition depends on the application for use. It is present at less than 100 parts by weight in a composition or in a suitable vehicle. The anti-adhesion agent is desirably present in an amount by weight of at least 0.01 parts per 100 parts of the composition. In a broad aspect, the anti-adhesion enzyme agent is present in an amount by weight of about 0.01 to about 10 parts by weight for every 100 parts by weight of total composition. More desirably it is at least 0.05 parts; and preferably 0.03 to 0.30 parts suitable for a paste composition.

One or more other antiplaque agents can be present in an antiplaque effective total amount. Suitable agents include without limitation stannous, copper, magnesium and strontium salts, dimethicone copolyols such as cetyl dimethicone copolyol, glucoamylase, glucose oxidase, urea, calcium lactate, calcium glycerophosphate, strontium polyacrylates and chelating agents such as citric and tartaric acids and alkali metal salts thereof.

The compositions may contain other additional agents and materials, including any desirable active or cosmetic agents and/or conventional oral care additives or excipients. For example, antibacterial agents may be present including benzethonium chloride, diisobutylphenoxyethoxyethyl dimethyl benzyl ammonium chloride, and cetyl pyridinium chloride as well as those listed in U.S. Pat. No. 5,776,435 to Gaffar et al., the contents of which are incorporated herein by reference.

The compositions of the invention may also include abrasives, such as silica or perlite; humectants, such as glycerin, sorbitol, xylitol, and/or propylene glycol; thickening agents, surfactants, a source of fluoride ions, a synthetic anionic polycarboxylate, a flavoring agent, antitartar agents, coloring agents, desensitizers (such as potassium nitrate), whitening agents, preservatives, silicones, and chlorophyll compounds. These additives, when present, are incorporated in the oral composition in amounts that do not substantially adversely affect the properties and characteristics desired.

The oral care composition of the invention may be prepared in any conventional manner. The preparation technique will necessarily vary depending ion the end delivery form desired, which may include any known for an oral care formulation, such as pastes, gels, suspensions, confectionaries (gum, candies, pastilles, and lozenges), tapes, films, rinses and washes, and tablets.

For example, a paste may be prepared as followed: the humectants (e.g., glycerin, sorbitol, propylene glycol, and polyethylene glycol) are dispersed in the water in a conventional mixer under agitation. Into the dispersion are added the enzyme or enzymes organic thickeners (such as xanthan gum), any anionic polycarboxylate, any salts (such as sodium fluoride anticaries agents), tetrasodium pyrophosphate, sodium tripolyphasphate anticalculus salts and any sweeteners; the resultant mixture is agitated until a homogeneous gel phase is formed. Into the gel phase are added a pigment (such as TiO$_2$) and any acid or base required to adjust the pH. These ingredients are mixed until a homogenous phase is obtained. The mixture is then transferred to a high speed/vacuum mixer; wherein, the inorganic silica thickener and surfactant ingredients are added to the mixture. The low oil absorption silica abrasive is added at this point, along with other abrasives to be used in the composition. The mixture is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The present invention provides useful formulations maintaining and stabilizing activity of the protease enzyme or at least minimizing loss of activity. Advantageously, antibacterial agents are combined with the protease enzyme in the formulation to provide synergistic results based on both anti-adhesion and antibacterial functionality. The functionality of the present inventive composition includes both anti-adhesion and plaque disruption actions. In one aspect, ficin is preferably selected for the former and papain is preferably selected for the latter. In another aspect, an anti-adhesion mode of action delivered an antiplaque efficacy in a human clinical study as exhibited by both ficin and papain, with ficin demonstrating greater efficacy than papain. The invention provides protease enzyme having activity of anti-adhesion for oral plaque bacteria and compositions suitable for oral treatment, which includes treatment vehicle having other functionalities that also stabilize the protease enzyme. In summary, the preferred protease enzyme derived from fig trees (ficin) demonstrated an anti-adhesion activity in simple solutions, in liquid dentifrices and in full pastes. The compound shows prevention of adhesion of bacteria single species and mixed culture species over negative controls onto polystyrene surfaces, Hydroxyapatite surfaces and real teeth. The compound furthermore shows an ability to modify tooth-like surfaces; namely, germanium prisms by reducing the surface energy of such surfaces. This compound can be used alone or as mixtures with other enzymes or antibacterial agents. The oral composition of the present invention is useable to treat any subject body having an oral cavity, including creature, human and animal; and the oral cavity encompasses mouth, tongue, tissue, teeth, palate and enamel, and the like. The oral composition may be brought into contact with the oral cavity in any of a variety of methods and is not limited to contact by any particular method. Examples include liquid vehicle, such as mouth rinse; paste vehicle, such as toothpaste; dentifrice; mouth beads and fresheners; chewing gum; toys; chewables; paint-on compositions and gels; consumables, edibles and confectioneries.

EXAMPLE I

Dentifrice Formulation Containing Anti-Adhesion Enzyme

Enzymes are formulated in a silica base formulation. Table 1 gives the exemplary dentifrice formulations. All values are weight percentages, unless otherwise indicated. Key formula ingredients of the formulation are enzymes, ficin, papain and krillase at 0.226% by weight, a mixed silica abrasive system for superior cleaning of 25% by weight, and a mixed surfactant system of 0.5% SLS/1.5% pluronic and 1% betaine, each by weight. A peppermint-spearmint flavor that is stable with enzymes is also included. The compositions are each selected to deliver attributes (such as foam, flavor, mouth feel and aesthetics) without compromising activity of enzymes. For the enzyme concentration, a dose response study targeted to select effective levels of enzymes was carried out prior to selecting the clinical formulations. Based on the in vitro studies, the clinical products were made in the OPTC (Oral Process Technology Center) under GMP conditions.

TABLE 1

Formulations of dentifrice containing enzymes

| INGREDIENT | Ficin | Papain | Krillase |
|---|---|---|---|
| 70% Sorbitol | 24.374 | 24.374 | 24.374 |
| 99.5% Synthetic Glycerin - USP | 20.0 | 20.0 | 20.0 |
| Purified Water | 17.0 | 17.0 | 17.0 |
| Dental Type Silica (Sylodent XWA 650 - USP) | 17.0 | 17.0 | 17.0 |
| Dental Type Silica (Zeodent 115) | 8.000 | 8.000 | 8.000 |
| Polyethylene Glycol 600 (PEG-12) NF | 3.000 | 3.000 | 3.000 |
| No. 2 Synthetic Amorph. Precipitated Silica - Zeodent 165 | 2.500 | 2.500 | 2.500 |
| 29% Sodium Lauryl Sulfate | 0.5 | 0.5 | 0.5 |
| Poloxomer 407 | 1.500 | 1.500 | 1.500 |
| Sodium CMC 2000S - 12 USP | 1.200 | 1.200 | 1.200 |
| Natural and artificial mixed spearmint | 1.100 | 1.100 | 1.100 |
| 30% Cocamidopropyl Betaine | 1.000 | 1.000 | 1.000 |
| Sodium Monofluorophosphate - USP | 0.760 | 0.760 | 0.760 |
| Tetrasodium Pyrophosphate - Fine (FCC) | 0.500 | 0.500 | 0.500 |
| Sodium Saccharin USP | 0.500 | 0.500 | 0.500 |
| Xanthan Gum - NF | 0.400 | 0.400 | 0.400 |
| POLY OXWSR-N 750 | 0.100 | 0.100 | 0.100 |
| BLUE POLY 50 | 0.300 | 0.300 | 0.300 |
| Blue color solution | 0.040 | 0.040 | 0.040 |
| Ficin | 0.226 | 0 | 0 |
| Papain | 0 | 0.226 | 0 |
| Krillase | 0 | 0 | 0.226 |
| TOTAL | 100 | 100 | 100 |

EXAMPLE II

Anti-Attachment Efficacy Study—Artificial Mouth

To test the efficacy of the actives in toothpaste formulas, saliva-coated hydropxyapatite (SHAP) disks served as the artificial teeth, and a bacteria culture consisting of the main oral bacteria in humans flowed through the system at a speed consistent with the in vivo human saliva. Eight disks for each treatment were then placed in the chemostat flow cell and oral bacteria culture was allowed to flow through the disks overnight (20-24 hours) to see if actives coated on the disk surfaces would prevent biofilm formation. After 24 hours the SHAP disks were removed and amount of bacteria quantified. The $ABS_{610}$ of the solutions were then measured and analyzed. This result gave an estimate of the amount of bacteria that were adhering on the SHAP disks. From this value, the percentage anti-adhesion effectiveness of the pastes is evaluated relative to a matching negative control. Two concentrations of protease were tested for each of the three protease; namely. 0.226 weight percent and 0.065 weight percent. The artificial mouth anti-adhesion experiment suggests that at the two concentrations tested for each of the three proteases, on average, all three had efficacy above that of the negative control pastes, which did not contain any of the enzyme. However, based on statistical analysis, the efficacy of krillase was not demonstrated. Papain and ficin showed efficacy at 0.226% concentration. Ficin showed similar efficacy at 0.065% and 0.226%. Based on these results, GMP batches for proof of concept clinical studies were prepared. The in vitro results showed that ficin was better then the papain, which was in turn better then the matching placebo paste.

EXAMPLE III

In Vivo Clinical Evaluation

Two human clinical studies were conducted to test the anti-adhesion efficacy of the products relative to matching negative control paste. The clinical procedure for measurement of anti-adhesion efficacy with the end benefit of reduced plaque is indicated below.

A. Modified Gingival Margin Plaque Index Determination (MGMPI)—Test Products 0.226% Ficin and Matching Negative Control Fifteen (15) in-house panelists were recruited and enrolled in this clinical study. Fourteen (14) panelists completed this three-week study. One panelist was dropped from the study due to minor illness that required antibiotic use. Panelists reported to the dental clinic for an oral examination and review of medical history. All acceptable panelists received a prophylaxis (dental cleaning) and started a one-week washout with Colgate Great Regular. During the treatment phase of the clinical study, the panelists reported to the dental clinic on their assigned morning. They received a full scaling and prophylaxis to remove all dental calculus and plaque. Disclosing solution was used during the procedure to verify complete removal of all plaque and calculus. Panelists then used 1.5 gm of the assigned dentifrice and then brushed for 60 seconds followed by rinse for 5 seconds with 10 ml of water. They were then instructed to refrain from all oral hygiene for 24 hours at the end of which they returned to the dental clinic rinsed with disclosing solution and had their plaque scored. Upon completion of the plaque score the panelists resumed normal oral hygiene (brushing whole mouth two times per day) using the washout product. Results are shown below.

| Plaque score (MGMPI) | Enzyme toothpaste (0.226% Ficin) | Matching Placebo toothpaste |
|---|---|---|
| Mean 24 hr. score | 14.55 ± 8.50* | 30.38 ± 17.99 |

*Statistically significant (p < 0.05) from placebo

A t-test was used to determine existing differences between products (p<0.05). The enzyme dentifrice (0.226% ficin) is statistically different from the matching placebo. The ficin-containing dentifrice showed a clinical plaque reduction by an anti-adhesion mode of action.

B. Modified Gingival Margin Plaque Index Determination (MGMPI)—Test Products 0.226% Papain and Matching Negative Control This clinical procedure was identical to that described above for ficin, except for the fact that 14 panelists were enrolled in this study all of whom completed the study.

| Plaque score (MGMPI) | Enzyme toothpaste (0.226% Ficin) | Matching Placebo toothpaste |
|---|---|---|
| Mean 24 hr. score | 17.07 ± 7.03* | 30.38 ± 17.95 |

*Statistically significant (p < 0.05) from placebo

A t-test was used to determine existing differences between products (p<0.05). The enzyme dentifrice (0.226% papain) is statistically different from the matching placebo. The papain-containing dentifrice showed a clinical plaque reduction by an anti-adhesion mode of action. Comparing the results for the two clinicals, it is further concluded that ficin-containing dentifrice showed a directionally better anti-adhesion efficacy then papain-containing dentifrice.

The GMP produced batches were aged for 6 weeks at 49° C. The enzyme activity of each of the enzymes was nearly unchanged compared to the initial activity numbers.

EXAMPLE IV

Dentifrice Formulation Containing Anti-Adhesion Enzyme and Antibacterial Agent

The procedure of Example I above is repeated, except that the amount of water is reduced and replaced with a corresponding amount of the exemplary antibacterial agent, CPC. Accordingly, water was reduced to 16.7 weight percent and CPC was included in an amount of 0.3 weight percent for each of the three formulations, as in Table 1.

We claim:

1. An oral composition comprising an anti-adhesion agent comprising ficin and papain, the anti-adhesion agent present in an amount effective to mitigate interaction between a subject oral cavity and plaque-forming material, wherein on the basis of 100 parts by weight of the oral composition the anti-adhesion agent is present in an amount of up to about 10 parts;
further comprising an antibacterial agent wherein the antibacterial agent comprises an alkyl pyridinium halide.

2. The composition of claim 1, wherein, on the basis of 100 parts by weight of the oral composition, the anti-adhesion agent is present in an amount of about 0.01 to about 10 parts.

3. The composition of claim 1, wherein, on the basis of 100 parts by weight of the oral composition, the anti-adhesion agent is present in an amount of at least 0.05 parts.

4. The composition of claim 1, wherein, on the basis of 100 parts by weight of the oral composition, the anti-adhesion agent is present in an amount of about 0.03 to about 0.3 parts.

5. The composition of claim 1, wherein the anti-adhesion agent comprises more than one cysteine protease.

6. The composition of claim 5, wherein the anti-adhesion agent additionally comprises krillase.

7. The composition of claim 1, which further includes at least one enzyme different from the cysteine protease.

8. The composition of claim 7, wherein the different enzyme is at least one selected from the group consisting of amylases, lipases, nucleases, and other proteases.

9. The oral composition of claim 1 having at least one antibacterial agent that includes cetyl pyridinium and at least one anti-adhesion protease enzyme that has a milk clotting activity greater than papain.

10. A method of reducing growth of plaque in an oral cavity of a subject comprising contacting the oral cavity with an effective amount of an anti-adhesion protease enzyme comprising ficin and papain, thereby mitigating interaction between the subject oral cavity and plaque-forming material, wherein on the basis of 100 parts by weight of the oral composition the anti-adhesion agent is present in an amount of up to about 10 parts; wherein the composition further comprises an antibacterial agent wherein the antibacterial agent comprises an alkyl pyridinium halide.

* * * * *